US00PP13005P2

(12) United States Plant Patent
Burrows

(10) Patent No.: US PP13,005 P2
(45) Date of Patent: Sep. 24, 2002

(54) HELICHRYSUM PLANT NAMED 'PROSPI'

(76) Inventor: John D. Burrows, 6 Shingay Lane, Sawston Cambridge (GB), Cb2 4SS ( * ) Notice: Subject to any disclaimer, the term of this patent is extended or adjusted under 35 U.S.C. 154(b) by 25 days.

(21) Appl. No.: 09/654,432

(22) Filed: Sep. 1, 2000

(51) Int. Cl.[7] ..... A01H 5/00
(52) U.S. Cl. ..... Plt./359

(58) Field of Search ..... Plt./359

*Primary Examiner*—Bruce R. Campell
*Assistant Examiner*—Susan B. McCormick

(57) ABSTRACT

A new and distinct cultivar of Helichrysum named 'Prospi' that exhibits insignificant flowers when compared to standard varieties and is characterized by its fine silver/green foliage and compact plant habit. These attributes in combination distinguish 'Prospi' from all other existing varieties.

3 Drawing Sheets

BOTANICAL CLASSIFICATION

*Helichrysum xambiguum.*

VARIETY DENOMINATION

'Prospi'.

CROSS-REFERENCES TO RELATED APPLICATIONS

This application is related to another application entitled Helichrysum Plant Named 'Prosil', Ser. No. 09/654,366, filed Sep. 1, 2000.

BACKGROUND OF THE INVENTION

The present invention relates to a new and distinct cultivar of *Helichrysum xambiguum* named 'Prospi'. The new plant was bred and selected in 1995 by the inventor in Sawston, Cambridge, Great Britain from seed that originated from unintroduced Helichrysum hybrids. Seedlings were grown out during the spring of 1995 and were selected for vegetative propagation based on a more compact plant habit and finer, denser, more vivid-colored foliage than other known cultivars of this type. The inventors breeding program is designed to enhance the foliage color of Helichrysum from the normal gray or dull green to brighter silver and pearl colors.

'Prospi' is distinguished by a more compact plant habit, finer foliage, and a dense foliage of vivid green and silver color. These combined characteristics distinguish 'Prospi' from all others that exist. In comparison, the only similar plant is Helichrysum 'Prosil', with a habit that is more dense and compact, exhibiting foliage that is silver rather than green and silver. The standard non-patented varieties of *Helichrysum angustifolium* have untidy foliage, dull and greener foliage, broader foliage and regular significant flowering. Compared to these 'Prospi' has tidy foliage, finer and brighter foliage of a silver/green color and insignificant yellow flowers when compared to those of standard varieties. Although 'Prospi' has reportedly flowered rarely in the UK the plant has flowered profusely in California during the second year in a 7-gallon container, but the flowers themselves are insignificant, and subsequent flowering has not yet been observed, but may be possible. Foliage and habit remain its most distinguishing features. The *Helichrysum*

*angustifolium* cultivar 'Dartington' (not patented) is compact but has darker foliage that is not fine-leafed. The new cultivar 'Prospi' was first asexually propagated in 1996 by the inventor in Rivenhall, Essex, Great Britain. Since the inventor's initial selection, the new variety has been repeatedly asexually reproduced by means of cuttings and has been found to remain firmly fixed in subsequent generations.

SUMMARY OF THE INVENTION

The following traits have been repeatedly observed and represent the characteristics of the new cultivar Helichrysum 'Prospi'. These attributes in combination distinguish this cultivar from all other varieties. Although 'Prospi' has a similar form and habit to 'Prosil', 'Prospi' is more open in habit and has a unique foliage color, that of silver and green. Compared to standard varieties such as *Helichrysum angustifolium*, the new variety 'Prospi' is more compact, tidier with finer foliage of a silver and green color and insignificant flowers that may only rarely flower.

BRIEF DESCRIPTION OF THE DRAWINGS

The accompanying colored photographs illustrate the overall appearance of the new cultivar.

Sheet 1 has two photos showing the entire plant and habit with blooms, from a front perspective.

Sheet 2 shows the foliage and habit of the entire plant, without blooms.

Sheet 3 compares 'Prospi' on the right, with 'Prosil' on the left illustrating the difference in habit and foliage color. All photographs are taken of plants grown in seven-gallon containers. The prints are made using conventional photographic techniques and although foliage colors in photographs may appear different from actual colors due to light reflectance, they are as accurate as possible by conventional photography.

BOTANICAL DESCRIPTION OF THE PLANT

The following is a detailed botanical description of the new Helichrysum cultivar 'Prospi'. Observations, measurements, values, and comparisons were collected in Encinitas, Calif. from 2 year old plants grown outdoors under prevailing conditions in seven-gallon containers.

The new Helichrysum plant has not been observed under all possible environmental conditions. The phenotype may vary with variations in environment such as temperature and light level, without, however, any variance in genotype. Color references are made to The 1995 Royal Horticultural Society Colour Chart except where general terms of ordinary dictionary significance are used. The growing requirements are similar to the species and no growing problems have been observed.

Botanical classification: Helichrysum 'Prospi'.
Common name: Licorice plant.
Parentage: A hybrid of *Helichrysum xambiguum.*
Propagation: Vegetative cuttings.
Rooting habit and time to develop: 3 weeks to root from cutting; 12 to 16 weeks to reach one-gallon size.
Plant form and growth habit: Compact, mounded
Type: Biennial/perennial sub-shrub.
Vigor: Vigorous.
Growth rate: Moderate, grows to 23.0 cm height in 22 weeks. Branching habit: Ascending, arching.
Hardiness: Zero degrees Centigrade.
Mature height and spread: 50 cm by 90 cm.
Stem color: 194D.
Stem shape: Cylindrical.
Stem length: 20 cm.
Stem diameter: 0.25 cm.
Internode length: 1 cm.
Stem surface: Tomentose.
Foliage:
*Leaf arrangement.*—Alternate.
*Shape.*—Linear.
*Leaf length.*—4.5 cm to 6 cm.
*Leaf width.*—4 mm.
*Margin type.*—Entire.
*Leaf base: Sheathing, cobweb-like surface at inside juncture.*
*Leaf tip.*—Acute.
*Leaf division.*—Simple.
*Surface.*—Tomentose.
*Upper leaf color* (*mature*).—148A and 191A.
*Lower leaf color* (*mature*).—148C and 194A.
*Upper leaf color* (*young*).—148B.
*Lower leaf color* (*young*).—148D.
*Petiole.*—None, semi-amplexicaul.
*Foliar fragrance.*—Slight spicy clove to anise scent.
Flower:
*Flowering season.*—Spring and summer.
*Inflorescence type.*—Flat umbel-like head, 30 to 40 flowers per umbel.
*Umbel dimensions.*—3.50 cm in diameter, 1.50 cm in height.
*Flower color* (*opening*).—7D.
*Flower color* (*open*).—13A.
*Fragrance.*—Licorice scented.
*Flower size.*—50 cm in diameter, 0.50 cm in height.
*Flower shape.*—Circular.
*Aspect.*—Erect, facing upward.
*Petals.*—Numerous, shape ovate, apex obtuse.
*Involucral bracts.*—Hairy, dry, color: yellow-white.
*Inner bracts.*—5.0 mm in length.
*Outer bracts.*—1.25 mm in length.
*Fruit.*—Angled, slightly compressed, hairless capsule.
*Seed.*—Dark brown with white glands.

I claim:

1. A new and distinct cultivar of *Helichrysum xambiguum* plant named 'Prospi' as described and illustrated.

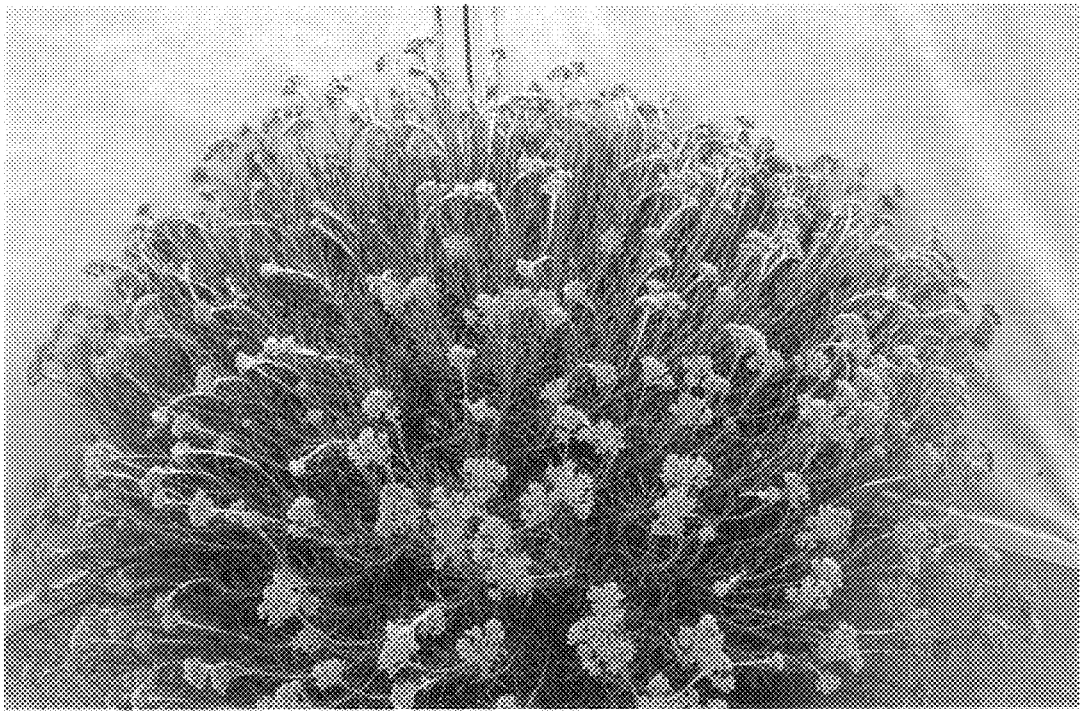
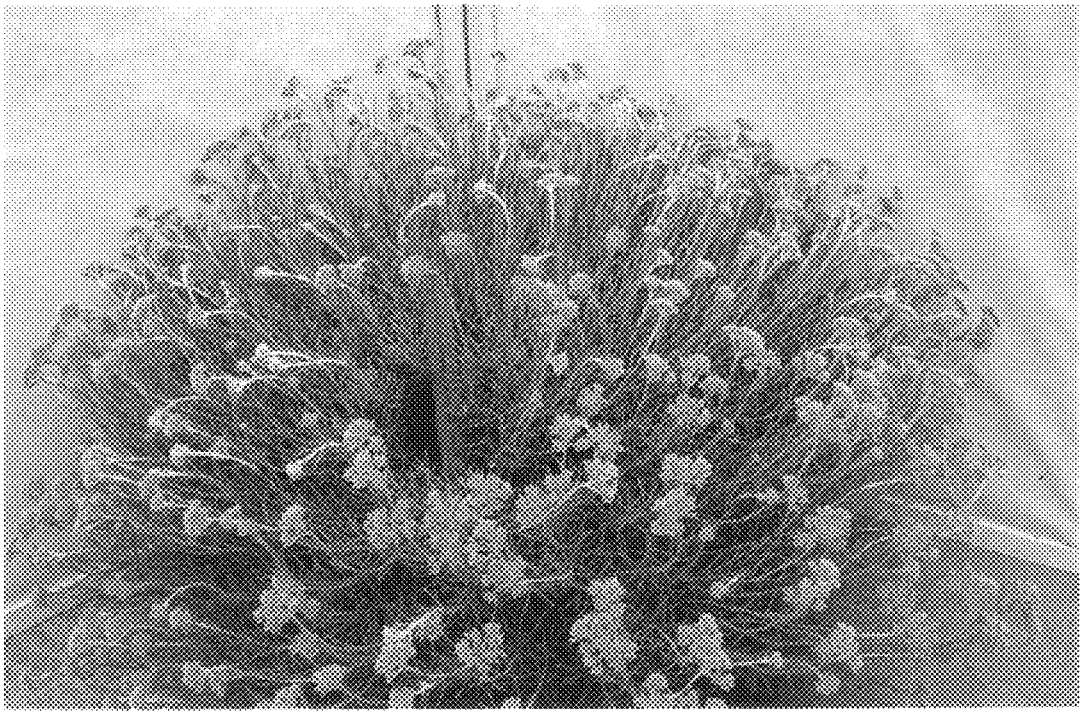

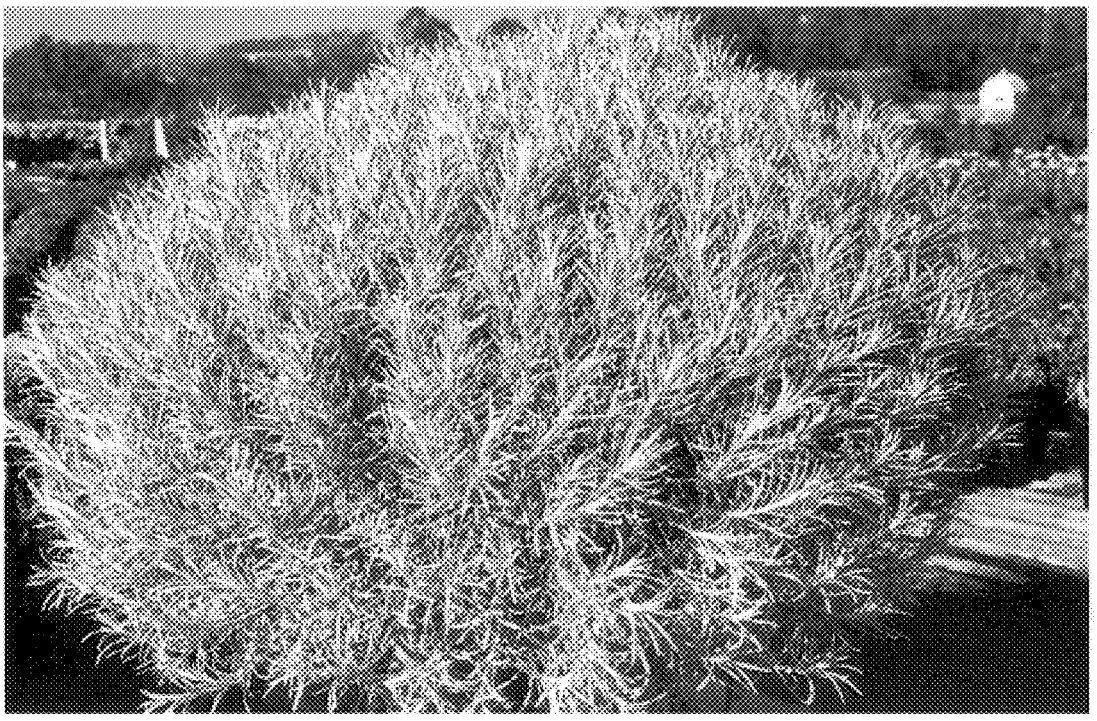

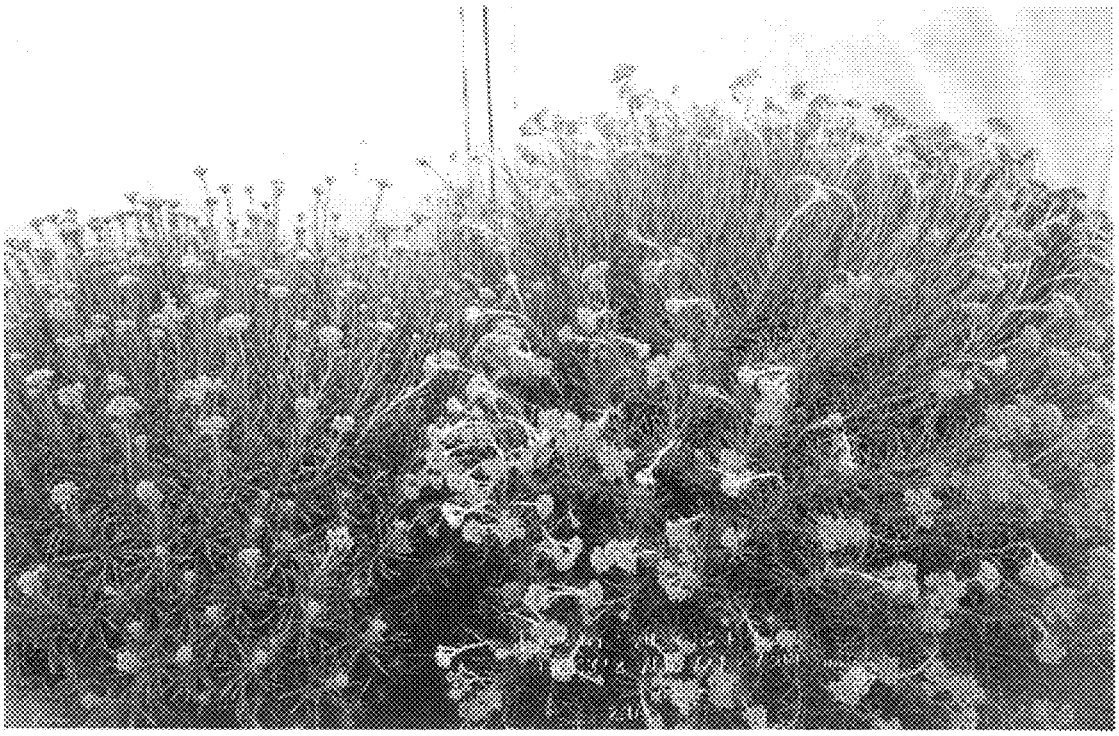

* * * * *